US007268216B2

(12) United States Patent  
Hytönen et al.

(10) Patent No.: US 7,268,216 B2  
(45) Date of Patent: Sep. 11, 2007

(54) CHIMERIC AVIDIN MUTANTS

(75) Inventors: Vesa Pekka Hytönen, Geifensee (CH); Olli Heikki Laitinen, Kuopio (FI); Henri Rainer Nordlund, Lempäälä (FI); Markku Sakari Kulomaa, Tampere (FI)

(73) Assignee: Licentia Oy, Helsinki (FI)

( * ) Notice: Subject to any disclaimer, the term of this patent is extended or adjusted under 35 U.S.C. 154(b) by 0 days.

(21) Appl. No.: 11/321,685

(22) Filed: Dec. 29, 2005

(65) Prior Publication Data

US 2006/0172387 A1    Aug. 3, 2006

(30) Foreign Application Priority Data

Dec. 31, 2004    (FI) .................................. 20041705

(51) Int. Cl.  
    *C07K 1/00*    (2006.01)
(52) U.S. Cl. ...................................... 530/350
(58) Field of Classification Search ................ 530/350, 530/388.21  
    See application file for complete search history.

(56) References Cited

FOREIGN PATENT DOCUMENTS

WO    WO-2004/018509    3/2004

OTHER PUBLICATIONS

Ahlroth et al., "Characterization and Chromosomal Localization of the Chicken Avidin Gene Family," *Animal Gen.*, 31:367-375 (2000).
Ahlroth et al., "Copy-Number Fluctuation by Unequal Crossing-Over in the Chicken Avidin Gene Family," *Biochem. and Biophy. Res. Comm.*, 288:400-406 (2001).
Backmann et al., "Thermodynamics and Kinetics of Unfolding of the Thermostable Trimeric Adenylate Kinase from the Archaeon *Sulfolobus acidocaldarius*," *J. Mol. Biol.*, 284:817-833 (1998).
Britton et al., "Structure Determination of the Glutamate Dehydrogenase from the Hyperthermophile *Thermococcus litoralis* and its Comparison with that from *Pyrococcus furiosus*," *J. Mol. Biol.*, 293:1121-1132 (1999).
Chilkoti et al., "Site-Directed Mutagenesis Studies of the High-Affinity Streptavidin-Biotin Complex: Contributions of Tryptophan Residues 79, 108, and 120," *Proc. Natl. Acad. Sci.*, 92:1754-1758 (1995).
Chu et al., "Thermodynamic and Structural Consequences of Flexible Loop Deletion by Circular Permutation in the Streptavidin-Biotin System," *Protein Sci.*, 7:848-859 (1998).
Clackson et al., "A Hot Spot of Binding Energy in a Hormone-Receptor Interface," *Science*, 267:383-386 (1995).
Delano, "Unraveling Hot Spots in Binding Interfaces: Progress and Challenges," *Structural Bio.*, 12:14-20 (2002).
Eisenberg-Domovich et al., "High-Resolution Crystal Structure of an Avidin-Related Protein: Insight into High-Affinity Biotin Binding and Protein Stability," *Acta Cryst.*, 61:528-538 (2005).

Ellison et al., "Limited Proteolysis of Native Proteins: The Interaction Between Avidin and Proteinase K," *Protein Sci.* 4:1337-1345 (1995).
Ferrin, et al., "The MIDAS Display System," *J. Mol. Graphics*, 6:36-37 (1988). only figures.
González et al., "Extremely High Thermal Stability of Streptavidin and Avidin Upon Biotin Binding," *BioMolec. Eng.*, 16:67-72 (1999).
Green, "Avidin and Streptavidin," *Methods in Enzymology*, 184:51-67 (1990).
Green, "Avidin," *Advances in Protein Chem.*, 29:85-133 (1975).
Hu et al., "Conservation of Polar Residues as Hot Spots at Protein Interfaces," *Proteins: Structure, Function, and Genetics*, 39:331-342 (2000).
Hyre et al., "Ser45 Plays an Important Role in Managing Both the Equilibrium and Transition State Energetics of the Streptavidin-Biotin System," *Protein Sci.*, 9:878-885 (2000).
Hytönen et al., "Chicken Avidin-Related Protein 4/5 Shows Superior Thermal Stability when Compared with Avidin while Retaining High Affinity to Biotin," *J. Bio. Chem.*, 279:9337-9343 (2004).
Hytönen et al., "Design and Construction of Highly Stable, Protease-Resistant Chimeric Avidins," *J. Bio. Chem.*, 280:10228-10233 (2005).
Hytönen et al., "Efficient Production of Active Chicken Avidin Using a Bacterial Signal Peptide in *Escherichia coli*," *Biochem. J.* 384:385-390 (2004).
Search Report for FI 20041705 dated Jun. 14, 2005.
Johnson et al., "Alignment and Searching for Common Protein Folds Using a Data Bank of Structural Templates," *J. Mol. Biol.*, 231:735-752 (1993).
Kannan et al., "Aromatic Clusters: a Determinant of Thermal Stability of Thermophilic Proteins," *Protein Eng.*, 13:753-761 (2000).
Klumb et al., "Energetic Roles of Hydrogen Bonds at the Ureido Oxygen Binding Pocket in the Streptavidin-Biotin Complex," *Biochemistry*, 37:7657-7663 (1998).
Knapp et al., "Crystal Structure of Glutamate Dehydrogenase from the Hyperthermophilic Eubacterium *Thermotoga maritima* at 3.0 Å Resolution," *J. Mol. Biol.*, 267:916-932 (1997).
Laitinen et al., "Biotin Induces Tetramerization of a Recombinant Monomeric Avidin," *J. Bio. Chem.*, 276:8219-8224 (2001).
Laitinen et al., "Chicken Avidin-Related Proteins Show Altered Biotin-Binding and Physico-Chemical Properties as Compared with Avidin," *Biochem. J.*, 383:609-617 (2002).

(Continued)

*Primary Examiner*—Maryam Monshipouri  
(74) *Attorney, Agent, or Firm*—Marshall, Gerstein & Borun LLP

(57) ABSTRACT

The present invention relates to new chimeric mutants of avidin protein with improved properties, e.g. thermostability, better stability against proteolysis, better charge properties (for example lower pI) compared to native avidin and avidin-related proteins, AVRs. The chimeric avidin mutants comprise mutants where a region or regions in avidin are substituted by a corresponding region or regions from an AVR protein.

6 Claims, 6 Drawing Sheets

OTHER PUBLICATIONS

Laitinen et al., "Mutation of a Critical Tryptophan to Lysine in Avidin or Streptavidin May Explain Why Sea Urchin Fibropellin Adopts an Avidin-Like Domain," *FEBS Letters*, 461:52-58 (1999).

Livnah et al., "Three-Dimensional Structures of Avidin and the Avidin-Biotin Complex," *Proc. Natl. Acad. Sci.*, 90:5076-5080 (1993).

Marttila et al., "Engineering of Chicken Avidin: A Progressive Series of Reduced Charge Mutants," *FEBS Letters*, 441:313-317 (1998).

Nardone et al., "Biochemical Characterization and Crystal Structure of a Recombinant Hen Avidin and its Acidic Mutant Expressed in *Escherichia coli*," *Eur. J. Biochem.*, 256:453-460 (1998).

Nordlund et al., "Enhancing the Thermal Stability of Avidin," *J. Bio. Chem.*, 278:2479-2483 (2003).

Sarkar et al., "The "Megaprimer" Method of Site-Directed Mutagenesis," www.pubmed.gov, Biotechniques, 8 (1990).

Serrano et al., "Aromatic-Aromatic Interactions and Protein Stability," *J. Mol. Biol.* 218:465-475 (1991).

Szilágyi et al., "Structural Differences Between Mesophilic, Moderately Thermophilic and Extremely Thermophilic Protein Subunits: Results of a Comprehensive Survey," *Structure*, 8:493-504 (2000).

Thompson et al., "Transproteomic Evidence of a Loop-Deletion Mechanism for Enhancing Protein Thermostability," *J. Mol. Biol.* 290:595-604 (1999).

Tuohimaa et al., "Development of Progestin-Specific Response in the Chicken Oviduct," *Int. J. Dev. Biol.*, 33:125-134 (1989).

Vetriani et al., "Protein Thermostability Above 100° C: A Key Role for Ionic Interactions," *Proc. Natl. Acad. Sci.*, 95:12300-12305 (1998).

Villeret et al., "The Crystal Structure of *Pyrococcus furiosus* Ornithine Carbamoyltransferase Reveals a Key Role for Oligomerization in Enzyme Stability at Extremely High Temperatures," *Proc. Natl. Acad. Sci.*, 95:2801-2806 (1998).

Wang et al., "Influence of the Carbohydrate Moiety on the Stability of Glycoproteins," *Am. Chem. Soc.*, 35:7299-7307 (1996).

Weber et al., "Structural Origins of High-Affinity Biotin Binding to Streptavidin," *Science*, 243:85-88 (1989).

Wilchek et al., "Foreword and Introduction to the Book (Strept)Avidin-Biotin System," *Elsevier Sci.*, 16:1-4 (1999).

Wilchek et al., "Introduction to Avidin-Biotin Technology," *Methods in Enzymology*, 184:5-13 (1990).

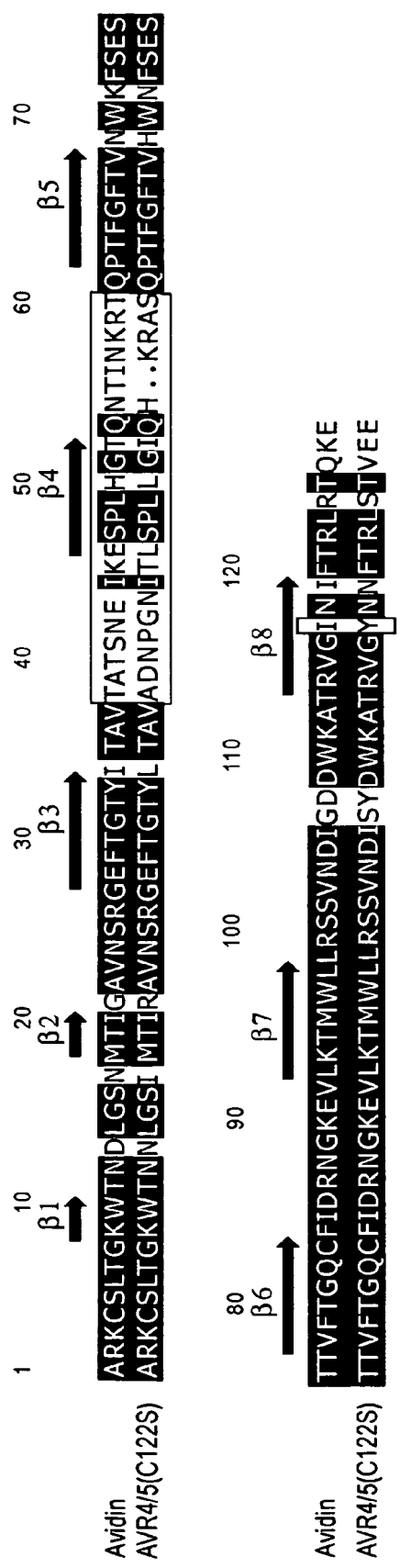
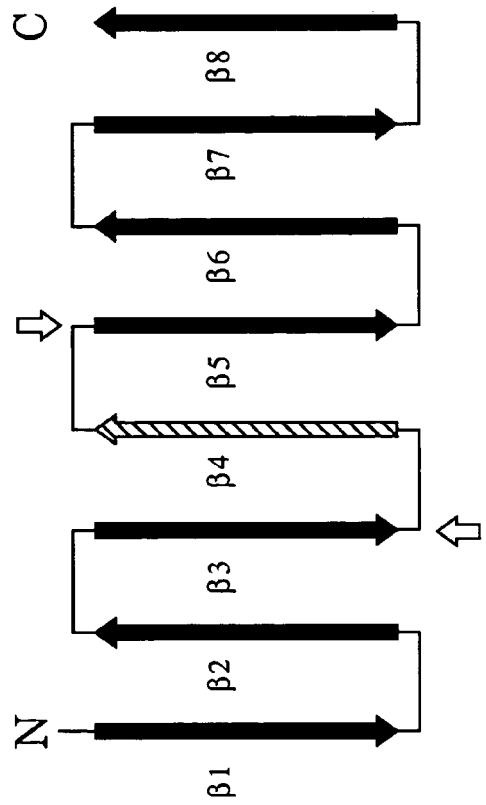
FIG. 1A
FIG. 1B

US 7,268,216 B2

CHIMERIC AVIDIN MUTANTS

FIELD OF THE INVENTION

The present invention relates to new chimeric mutants of chicken avidin protein with improved properties, e.g. thermostability, better stability against proteolysis, better charge properties (for example lower pI) compared to native avidin and avidin-related proteins, AVRs. The chimeric avidin mutants comprise mutants where a region or regions in avidin are substituted by a corresponding region or regions from an AVR protein.

BACKGROUND OF THE INVENTION

Avidin is a homotetrameric glycoprotein isolated from chicken egg-white. Each of the eight-stranded beta-barrel subunit of avidin consists of 128 amino acids and has one ligand-binding site. Avidin, like its bacterial analogue streptavidin from *Streptomyces avidinii*, is able to form a tight and specific complex with a water-soluble vitamin, d-biotin (dissociation constant $K_d \approx 10^{-15}$ M) (1,2). This special property of avidin together with its tetrameric nature and high stability have made it one of the most widely exploited protein tools in the life-sciences across a range of biochemical, pharmaceutical and biophysical applications (3,4).

The avidin gene family consists of avidin and seven avidin-related genes (AVRs) (5). Although avidin protein is expressed in various tissues (6), the other members of the gene family have not so far been found in the form of proteins in the chicken. In order to study their functional and structural properties, AVR proteins were recently produced by a baculovirus insect cell expression system (7). Genes AVR4 and AVR5 both encode identical protein, called AVR4/5. Avidin and AVR4/5 are about 80% identical in amino acid sequence, and almost all of the residues involved in biotin binding in avidin are conserved in AVR4/5. It was found that recombinant AVR4/5 bound biotin almost as tightly as avidin. Most interestingly, it was shown to be significantly more thermostable, the transition midpoint of heat denaturation $T_m$ being 106.4° C. compared to that of avidin, which $T_m$ is 83.5° C. (8).

It has been proposed that protein oligomerization in nature serves to obtain more stable structures (9,10). In addition, stable proteins tend to have only a few intrinsic water clefts in their structures (11,12). Moreover, the role of ionic bonds in establishing the high thermal stability of proteins has been studied by Szilágyi and Závodszky (13), who performed a statistical analysis of high-quality protein structures obtained from mesophilic and thermophilic organisms. They observed a correlation between the number of ion pairs and growth temperature of the organism, and hypothesized that ion pairs have structural importance especially at high temperatures. The ionic bonds found in thermostable proteins have successfully been transferred to their analogues from mesophilic organisms in order to stabilize them (14). The importance of aromatic pairs in thermostable proteins has also been noticed (15), and these pairs have successfully been transferred between proteins to improve the thermal stability (16).

SUMMARY OF THE INVENTION

The chicken avidin gene family consists of avidin and seven separate avidin related genes (AVRs) 1-7 (SEQ ID NOs:2-8). Avidin protein is a widely used biochemical tool whereas the other family members have only recently been produced and characterized as recombinant proteins. Previously, AVR4/5 has been found to be the most stable biotin-binding protein thus far characterized ($T_m$=106.4° C.). The high-resolution structure of AVR4/5 facilitated comparison of the structural details of avidin and AVR4/5. In the present invention, the information obtained from these comparative studies is used to transfer the stability and functional properties of AVR4/5 to avidin. In the present invention higher thermal stability and also better stability against proteolytic degradation were obtained. There are some interesting properties in AVR proteins and it may be possible to move these to the avidin using analogous strategy.

A chimeric avidin protein, ChiAVD, containing a 21 amino acid segment of AVR4/5 was found to be significantly more stable ($T_m$=96.5° C.) than native avidin ($T_m$=83.5° C.), and its biotin-binding properties resembled those of AVR4/5. Optimization of a crucial subunit interface of avidin by an AVR4/5-inspired point mutation of isoleucine 117 to tyrosine (I117Y) significantly increased the thermostability of the avidin mutant ($T_m$=97.5° C.) without compromising its high biotin-binding properties. By combining these two modifications, a hyperthermostable ChiAVD(I117Y) was constructed ($T_m$=111.1° C.). We also studied further the biotin-binding properties of AVR4/5. An increase in the energy barrier between the biotin-bound and unbound state of AVR4/5 was observed when compared to that of avidin. The chimeras thus obtained may find a role in applications utilising extreme conditions, like PCR.

BRIEF DESCRIPTION OF THE FIGURES

FIG. 1 A) Needleman-Wunsch alignment of chicken avidin (SEQ ID NO:17) and AVR4/5 (SEQ ID NO:18). The identity of the proteins is 77.8%. The area covering beta-sheet 4 and parts of its surrounding loops are boxed as well as the mutated amino acid residue I117. The alignment was made using MALIGN (36). B) Topology diagram of the chimeric protein. The segments taken from avidin are shown in black and the part inserted from AVR4/5 is shown in gray. The boundaries between these segments are highlighted by white arrows.

The arrow shows the location of digested protein forms. The sampled marked with "c" are control samples without protease treatment. A=avidin+ProtK, Y=AVD(I117Y), 4=AVR4/5(C122S), C=ChiAVD, CY=ChiAVD(I117Y), 4b=AVR4/5(C122S)-b. The marker proteins with molecular weights of 14.4, and 21.5 kDa are shown in figure.

Figure 4:
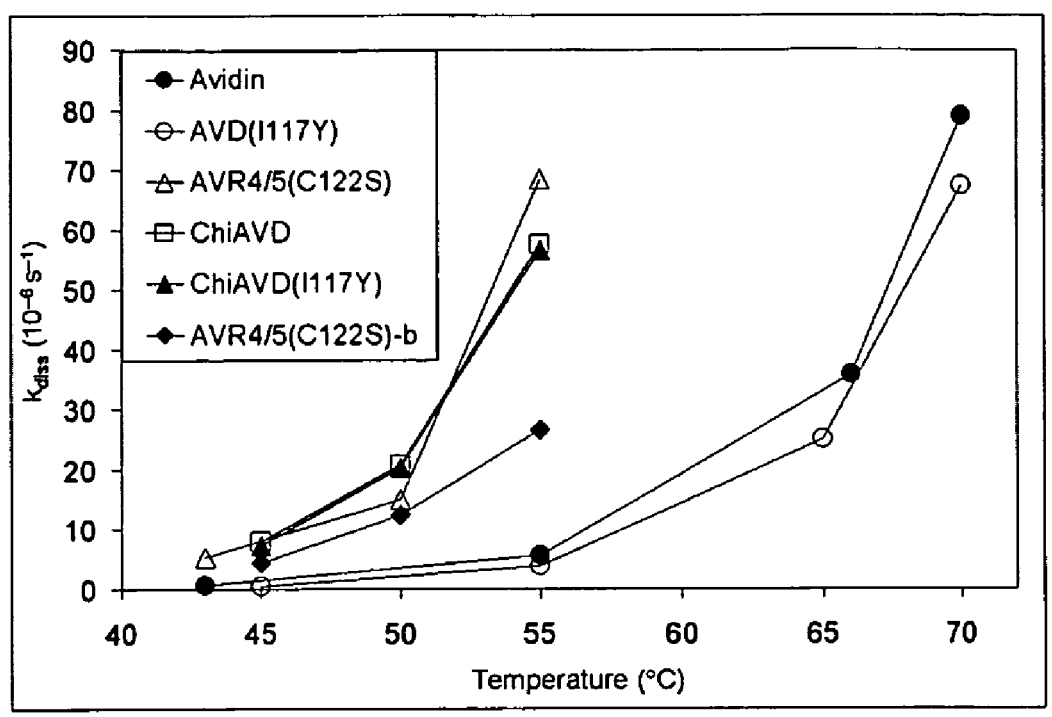

FIG. 4 Radiobiotin dissociation rate constants measured for the proteins as a function of temperature. The dissociation rate constants determined by global fitting are connected by lines.

Figure 5:
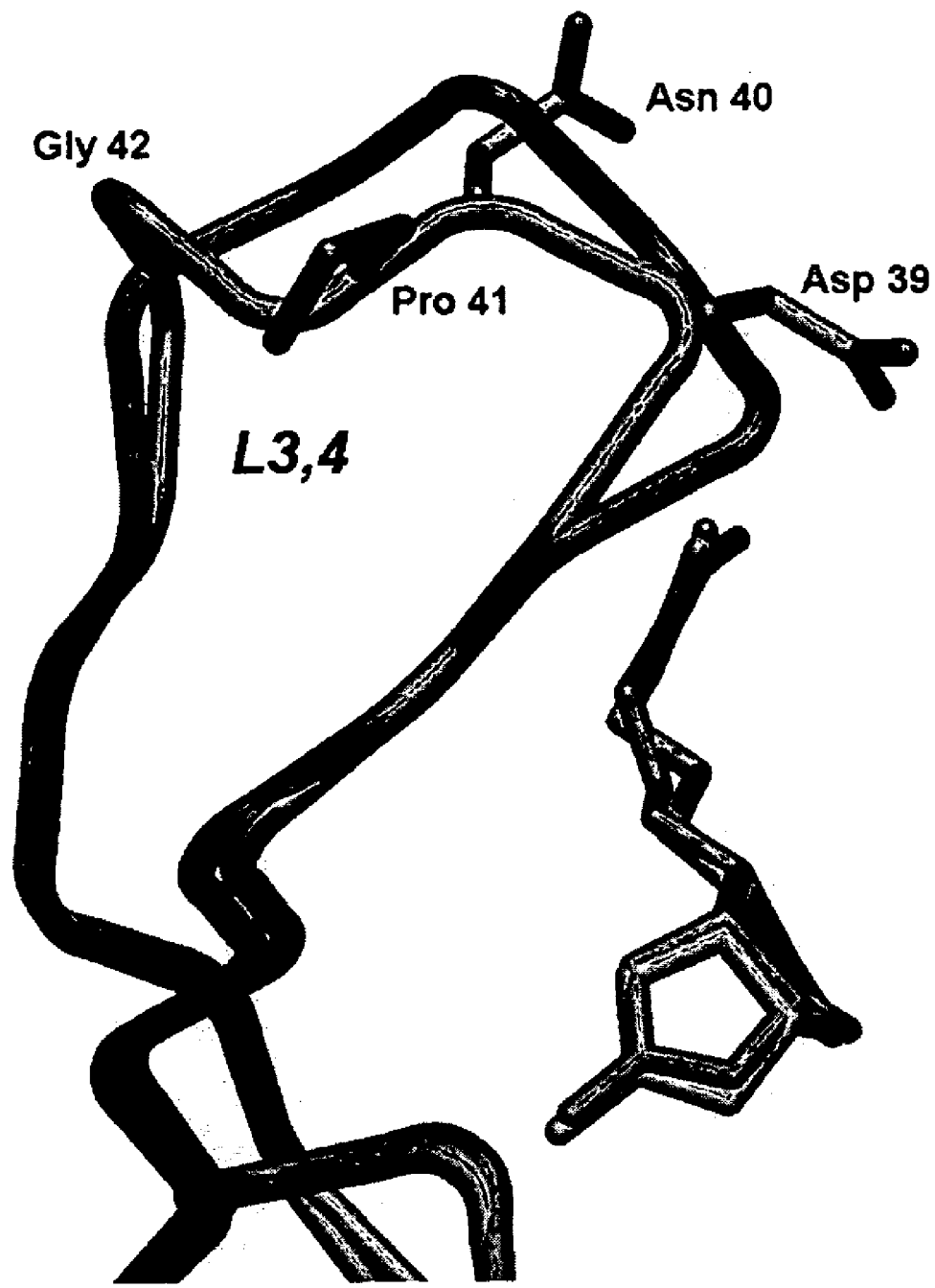

FIG. 5 Tube representation of the superposition of the avidin (magenta) and AVR4/5 (cyan) in the L3,4 loop region with biotin molecules in the binding site for reference. The side chains of residues 39 to 42 are shown for AVR4/5 and indicate the kink in the loop induced by the Pro-Gly tandem. Although the L3,4 loops in both proteins are of the same size, they adopt an entirely different conformation. The closed conformation of L3,4 in the AVR4/5 is apparent in both the apo and biotin complex forms. The figure was constructed using MIDAS (37).

Figure 6:
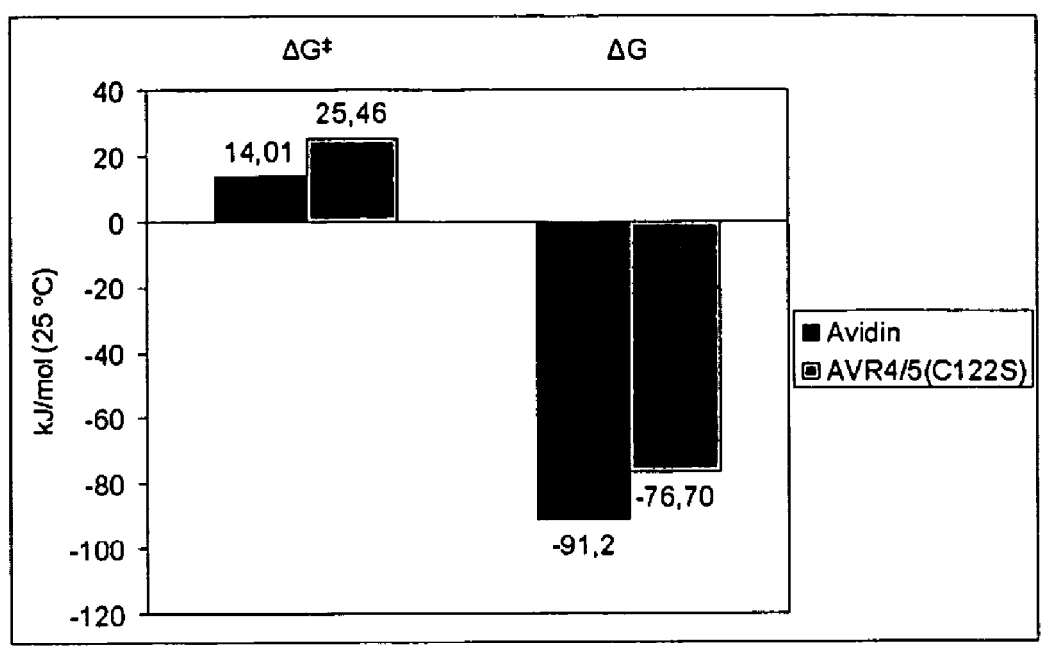

FIG. 6 Reaction thermodynamic coordinates for biotin binding to avidin and AVR4/5(C122S). The activation energy of dissociation obtained from the Eyring equation fitted to the dissociation data was used to calculate the transition state energy ($\Delta G\ddagger$) for the reaction, using the total binding energy values ($\Delta G$) previously determined for binding (8).

DETAILED DESCRIPTION OF THE INVENTION

The chicken avidin gene family consists of avidin and seven separate avidin related genes (AVRs) 1-7. AVR4/5 has been found to be the most stable biotin-binding protein thus far characterized ($T_m$=106.4° C.). The objective of the present invention was to identify the features that make AVR4/5 so much more stable protein than chicken avidin (8), and to transfer this higher stability to avidin. Another objective of the invention was to explore and compare the biotin-binding properties of avidin, AVR4/5 and the chimeric proteins produced in this invention. A further objective was to determine the importance of the differences in the primary and three-dimensional structures (Eisenberg-Domovich et al., manuscript) of these proteins for their biotin-binding and stability properties (8). To accomplish these objectives, molecular modeling and the solved three-dimensional structures were utilized and the results used to transfer the stabilising elements from AVR4/5 to avidin. On the basis of the sequence comparison made between avidin and AVR4/5, the highly variable segment between the two proteins is located between L3,4 and L4,5 (FIG. 1). Firstly, a chimeric avidin was engineered, in which a β4 and its adjacent loops were replaced by the corresponding region from AVR4/5. The thermal stability of the resultant chimera was clearly higher ($T_m$=96.5° C.) than that of avidin ($T_m$=83.5° C.) but lower than that of AVR4/5 ($T_m$=106.4° C.).

In another mutant, a point mutation (I117Y) was introduced into avidin from the AVR4/5 sequence on the basis of the modeling (8) and 3-D X-ray structure analysis (Eisenberg-Domovich et al., manuscript), which was thought to play an important role in the intersubunit interactions and thus contribute to the thermal stability of AVR4/5. This substitution raised the thermal stability of the mutant thus obtained to a level ($T_m$=97.5° C.) comparable to that of the above-described chimera. Furthermore, when the two modifications were combined, a hyperthermostable avidin showing even greater thermal stability ($T_m$=111.1° C.) than AVR4/5 was achieved.

As expected, a significantly more stable protein was obtained when a 21-long amino acid segment (residues 38-58) taken from AVR4/5 was transferred to avidin by substituting the residues 38-60 of the avidin molecule. The shortening of the L4,5 loop by two residues in the chimeric avidin (ChiAVD) may provide a partial explanation for the higher stability. By comparing genomes of mesophiles, thermophiles and extremophiles, Thompson and Eisenberg found shorter exposed loops from temperature-resistant proteins when compared to those of their mesophilic analogues (25). The L3,4 loop, however has the same length in avidin and AVR4/5, yet its amino acid composition is entirely different (FIG. 1). The three-dimensional structure of L3,4 clearly shows that it has a different conformation in AVR4/5 than in avidin (FIG. 5) (Eisenberg-Domovich et al., manuscript). It is assumed that ChiAVD and AVR4/5 share a similar L3,4 loop conformation. The presence of the Pro41-Gly42 stretch and the salt bridge between Asp39 and Arg112 induces stability in the L3,4 loop in both the apo and biotin complex forms (Eisenberg-Domovich et al., manuscript).

The importance of certain stability "hot-spot" residues in protein interfaces has been noticed (26-28). Aromatic pairs are known to form stabilizing pairs in protein structures, which have also been studied experimentally (16). In the present invention, the subunit interface of avidin was optimised by replacing Ile117 residue with tyrosine according to the AVR4/5 sequence. The previous modeling analysis (8) suggested that tyrosine in this location is able to improve the stability of the AVR4/5 tetramer as compared to that of avidin. The three-dimensional structure of AVR4/5 indicates the presence of π-π (pii-pii) stacking between two tyrosine residues from neighbouring monomers (Eisenberg-Domovich et al., manuscript) and experimental data (AVD(I117Y), $T_m$=97.5° C.; avidin, $T_m$=83.5° C.) support the improved structure at this site. Kannan and Vishveshwara compared the aromatic clusters in proteins from thermophilic and mesophilic organisms (15). They found that residues comprising aromatic clusters in proteins from thermophilics are preferably replaced by Leu or Ile in proteins from mesophilic organisms.

It should be noted that more than one point mutation could be introduced to the protein. In an earlier application FI 20031663, which is incorporated here as reference, new thermally stabilized biotin binding proteins were constructed using site-directed mutation. For avidin and AVRs this was achieved by introducing disulphide bridges between its subunits.

From the stability point of view the most interesting result was that combination of the chimera approach and the I117Y point mutation produced a protein that was even more thermostable than AVR4/5. This indicates that the structural factors that account for the difference in stability between avidin and AVR4/5 have successfully been recognized and transferred. It has been proposed earlier that recombination inside the avidin gene family is a frequent event (29). The results in the present application indicate, that recombination may produce functional chimeric proteins inside the gene family, since building blocks moved from AVR4/5 seem to be able to function as part of the avidin structure without negative implications.

The enhancement of the stability in ChiAVD is due to substitution of region between beta strands 3 and 5 from AVR4/5. The other AVRs have fairly similar sequence in this region with AVR4/5 and the movement of any of these regions to avidin may allow stabilisation of the end-product similarly as in the case of ChiAVD.

For example, avidin has an isoelectric point at high pH i.e it is basic protein. Instead, AVR2 is acidic protein having pI close to pH 5. Therefore, one may be able to change the pI of avidin by moving parts of avidin related proteins to avidin. Simultaneously one could obtain better stability of the end product when compared to wild type avidin.

The isoelectric point of avidin was previously lowered by genetic methods by Marttila et al. (38) and Nardone et al. (39), but only individual amino acids were replaced in these studies.

The invention will be further described with reference to the following non-limiting examples.

EXAMPLES

Example 1

Construction, Purification and Sequence Analysis of Chimeric Avidin Mutant

In order to study the significance of the differing segment between β3 and β5, a ChiAVD (SEQ ID NO:15) was constructed in which this segment was transferred from AVR4/5 (SEQ ID NO:5/SEQ ID NO:6) to avidin (SEQ ID NO:1). The amino acid residues 38-60 of avidin were substituted by 38-58 amino acid residues from AVR4/5 (FIG. 1). Furthermore, isoleucine 117 in avidin was mutated to tyrosine according to AVR4/5 (FIG. 1).

Chimeric ChiAVD protein was produced by three sequential PCR reactions, in which the final product was obtained from partially overlapping megaprimer (17) products. The oligonucleotides Kimera.1 and Kimera.2 were used in the first PCR with AVR4 cDNA (7) (SEQ ID NO:5) as a template. The product was isolated by agarose gel electrophoresis and used as a megaprimer in the following PCR with oligonucleotide AK33. Avidin cDNA was used as a template in the second PCR. The product was again isolated by electrophoresis and used again as a megaprimer in the third PCR with oligonucleotide AK44. Avidin cDNA was used as a template in the third PCR. The product was isolated by electrophoresis.

The obtained DNA was digested by BgIII and HindIII and ligated to the BamHI/HindIII-digested pFASTBAC1-plasmid. The final product was confirmed by DNA sequencing.

Mutation I117Y was made to pFASTBAC1 plasmid coding for avidin or ChiAVD by QuickChange (Stratagene, La Jolla, Calif., USA) method using oligonucleotides I117Y.1 and I117Y.2. The final product was confirmed by DNA sequencing as ChiAVD(I117Y) (SEQ ID NO:16).

The final product was cloned to the pFASTBAC1 vector. Recombinant baculoviruses coding for ChiAVD forms, AVR4/5(C122S) and AVD(I117Y) were generated as instructed by the manufacturer of the Bac-To-Bac™ system (Invitrogen). Proteins were produced in baculovirus-infected Sf9 insect cells, in biotin-free medium as reported earlier (7). Non-glycosylated AVR4/5(C122S)-b was produced using the E. coli expression system (18) (Laitinen et al., unpublished) in order to study the influence of the carbohydrate chains on the properties of the protein (Table I). The proteins were then purified by affinity chromatography using 2-iminobiotin agarose, as previously described (19). The protein forms are summarised in Table I.

Sequences of oligonucleotides:

```
Kimera.1
GCACCTACATCACAGCCGTAGCGGATAATCCAGGAAA
(SEQ ID NO:9)

Kimera.2
GAAGCCAAAGGTGGGCTGGCTGGCTCTTTTGTGTTGG
(SEQ ID NO:10)

AK33
CT GCT aga tct ATG GTG CAC GCA ACC TCC CC
(SEQ ID NO:11)

AK44
GTTGCAAGCTTTGCGGGGCCATCC
(SEQ ID NO:12)

I117Y.1
```

```
CAGGGTCGGCTACAACATCTTC
(SEQ ID NO:13)

I117Y.2
GAAGATGTTGTAGCCGACCCTG
(SEQ ID NO:14)
```

TABLE I

Description of proteins analysed.

| Protein | Modifications | Source |
|---|---|---|
| AVD | — | Chicken[a] |
| AVD(I117Y) | Mutation I117Y in 1-3 subunit interface. | BEVS[b] |
| ChiAVD | Residues 38-58 moved from AVR4/5 to avidin. | BEVS[b] |
| ChiAVD(I117Y) | Residues 38-58 moved from AVR4/5 to avidin and mutation I117Y in 1-3 subunit interface. | BEVS[b] |
| AVR4/5(C122S) | Cysteine residue forming intermonomeric disulphide bridges in AVR4/5 mutated to serine. | BEVS[b] |
| AVR4/5(C122S)-b | As above but non-glycosylated. | E. coli[c] |

[a]Chicken avidin obtained from Belovo S. A. (Bastogne, Belgium).
[b]Recombinant protein produced by baculovirus expression vector system in insect cells.
[c]Recombinant protein produced by bacterial expression system. This form contains three additional residues (Gln-Thr-Val) in the N-terminus from the bacterial signal peptide (18).

Figure 2:
FIG. 2 SDS-PAGE analysis of the purified proteins. A=avidin, Y=AVD(I117Y), C=ChiAVD, CY=ChiAVD (I117Y), 4=AVR4/5(C122S), 4b=AVR4/5(C122S)-b produced in bacteria. The marker proteins with molecular weights of 14.4, 21.5 and 31 kDa are shown in figure.

Isolated proteins showed high purity in SDS-PAGE analysis (FIG. 2). The glycosylation patterns of the purified proteins differed since AVR4/5(C122S) has three potential glycosylation sites whereas avidin has only one (1,7). One of these sites (Asn43) of AVR4/5 was transferred to the chimeric protein, resulting in more extensive glycosylation of the chimera when compared to that of native avidin. Bacterially produced AVR4/5(C122S) was non-glycosylated as expected (FIG. 2).

The sequence identity between avidin and AVR4/5 is 77.8%. More than half (15 of 28 mutations) of the differences between these two proteins are found on the relatively short 23/21 (avidin/AVR4/5) amino acid segment between the end of β3 and the beginning of β5 (FIG. 1). All residues showing contact with biotin (24) are conserved, excluding the Thr38-Ala39-Thr40-sequence located in the L3,4 loop (connecting β3 and β4 strands), which is replaced by Ala38-Asp39-Asn40 in AVR4/5. Subunit interface residues (41 residues) (8) are also well-conserved, the only amino acid differences being Thr38Ala, Ala39Asp, His50Leu, Thr52Ile, Asn54His and Ile117Tyr (numbering according to avidin sequence).

Example 2

Proteinase K Assay

The proteolytic resistance of the proteins were studied using proteolysis by Proteinase K, as previously described (7). Protein sample (4 μg) was incubated in the presence of Proteinase K (1/25 w/w) at 37° C. for a predetermined time period, denatured by boiling in sample buffer (SDS, 2-mercaptoethanol) and subjected to SDS-PAGE followed by coomassie staining.

Figure 3:
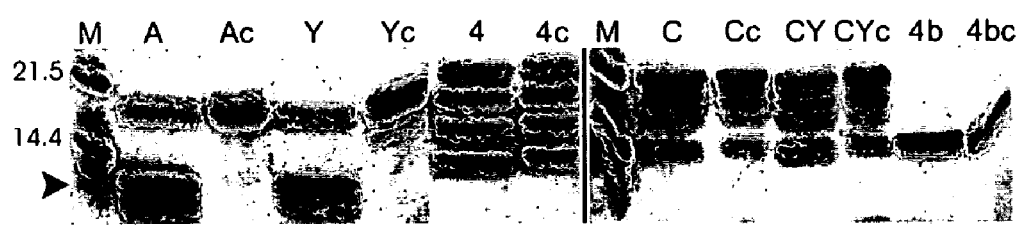
FIG. 3 SDS-PAGE analysis of protein samples incubated with Proteinase K.

Avidin and avidin mutant AVD(I117Y) were found to be 50% digested after treatment for 16 hours with Proteinase K (FIG. 3). When these proteins were saturated with biotin before treatment, no cleavage was observed. AVR4/5

(C122S), however, displayed total resistance to the proteolytic activity of Proteinase K, even without biotin. ChiAVD, ChiAVD(I117Y), as well as AVR4/5(C122S)-b produced in E. coli, were also found to behave as AVR4/5 (C122S) in this assay, i.e. remaining intact for 16 hours in the presence of protease in the presence or absence of biotin. This indicates that the conformation of L3,4 of the AVR4/5 apoprotein (Eisenberg-Domovich et al., manuscript) protects it from digestion. Furthermore, glycosylation in residue Asn43 (8) did not seem to play a role in the protease resistance.

Proteinase K cleaves avidin in only one region in the loop between β-strands 3 and 4 (33). It was also found that biotin efficiently inhibits the cleavage. On the other hand, AVR4/5 and streptavidin are resistant to cleavage by Proteinase K, even without bound biotin (8,32). Since Proteinase K cleaves a variety of sequences, the explanation for the resistance to cleavage might lie in the conformation of the L3,4 loop of AVR4/5. The Proteinase K resistance of ChiAVD supports these results (FIG. 3). The different loop structure can be seen in the structure of AVR4/5 (FIG. 5) (Eisenberg-Domovich et al., manuscript). Proline in this loop seems to cause bending in the middle of the loop. Accordingly, the corresponding loop in streptavidin is three residues shorter (34), and may not, therefore, be accessible to the protease. No difference between the glycosylated and non-glycosylated form of AVR4/5(C122S) was observed in this analysis; hence, the sugar moiety in this loop in AVR4/5 cannot explain the resistance to the protease. This is also true for avidin, which showed similar stability in both the enzymatically deglycosylated and normal carbohydrate-containing forms (35).

Example 3

Gel Filtration Analysis

The oligomeric state of the proteins was assayed with FPLC gel filtration as previously described (8). Sodium carbonate buffer (50 mM, pH 11) with 150 mM NaCl was used as the liquid phase. Protein samples of 5-10 µg were used in the analysis.

All the engineered proteins showed tetrameric appearance when subjected to gel filtration analysis. Bacterially produced AVR4/5(C122S) showed a slightly lower apparent molecular weight as compared to the other proteins, as expected, owing to the lack of the carbohydrate moiety (Table II).

Example 4

Microplate Assay

The inactivation of the proteins during heat-treatment was analysed by using a microplate assay (23). The proteins were heated to 99.9° C. in 50 mM phosphate buffer containing 100 mM NaCl (pH 7.0) for 32 minutes. The remaining activity was probed by measuring the ability of the proteins to bind biotinylated alkaline phosphatase by coating the microplate wells with samples of the heated proteins.

The remaining activity after treatment for 32 minutes is shown in Table II. These results are in line with DSC analyses showing that ChiAVD(I117Y) is the most thermally stable of the proteins characterised.

Example 5

Differential Scanning Calorimetry (DSC)

The transition midpoint of the heat denaturation ($T_m$) of the avidin proteins was studied using a Calorimetry Sciences Corporation (CSC) Nano II differential scanning calorimeter, as in previous reports (22,23). Proteins (~0.5 mg/ml) were analyzed both in the absence and presence of biotin (3:1 molar ratio; biotin:avidin monomer).

In the DSC-experiments the ChiAVD protein and AVD (I117Y) showed significantly better thermal stability than avidin both as apoforms and holoforms (Table II). When these modifications were combined, the resultant ChiAVD (I117Y) was found to be even more stable than AVR4/5 (C122S). In all cases holoforms were clearly more stable than apoforms. We observed a significant increase in the unfolding enthalpy with an increasing melting temperature. AVR4/5(C122S)-b showed similar behavior as compared to the protein produced in insect cells in the DSC analysis.

TABLE II

Structural properties of avidins. FPLC gel filtration elution times and calculated molecular weights of the proteins. Heat-induced unfolding of proteins determined by DSC (average ± S.D).

| Protein | Gel filtration | | DSC[c] | | | | Microplate assay |
|---|---|---|---|---|---|---|---|
| | Elution time (min) | Molecular mass (kDa) | $T_m$(-biotin) (° C.) | $T_{m(+biotin)}$ (° C.) | $\Delta T_m$[a] (° C.) | $\Delta H$[b] (kJ/mol) | Activity[e] (%) |
| AVD | 29.3 | 53.1 | 83.5 ± 0.1 | 117.0 ± 0.7 | 33.5 | 329 ± 5 | 4 |
| AVD(I117Y) | 29.6 | 49.5 | 97.5 ± 0.4 | 123.7 ± 0.1 | 26.2 | 536 ± 6 | 47 |
| ChiAVD | 29.0 | 56.9 | 96.5 ± 0.2 | 124.4 ± 0.2 | 27.9 | 527 ± 10 | 47 |
| ChiAVD(I117Y) | 29.0 | 56.9 | 111.1 ± 0.2 | ~130[d] | ~19 | 659 ± 38 | 98 |
| AVR4/5(C122S) | 29.5 | 50.6 | 106.4 ± 0.8 | 125.4 ± 0.8 | 19.5 | 575 ± 33 | 72 |
| AVR4/5(C122S)-b | 30.3 | 42.1 | 109.9 | 127.1 | 17.2 | 460 | 56 |

[a]$\Delta T_m$ is the change in $T_m$ upon addition of a three-fold molar excess of biotin.
[b]$\Delta H$ value obtained from sample without biotin. The value could not be determined accurately from samples saturated with biotin because the $T_m$ values were too close to the temperature limit of the DSC instrument.
[c]The results of AVD and AVR4/5(C122S) are from (8).
[d]Could not be determined accurately due to upper limit of temperature of the DSC instrument.
[e]Biotin-binding activity after 32 min treatment at 99.9° C.

Example 6

Optical Biosensor Studies

The biotin-binding characteristics of the different avidins were studied by a surface plasmon resonance (SPR) optical biosensor (IAsys). The binding affinities to the 2-iminobiotin surface in 50 mM borate buffer (pH 9.5, 1 M NaCl) were measured as previously reported (7). The result are shown in table III.

TABLE III

2-Iminobiotin-binding properties of proteins determined by IAsys optical biosensor. Iminobiotin-binding properties of the proteins analysed by an IAsys optical biosensor at 20° C. Affinities to 2-iminobiotin surface are determined from the equilibrium response data. $k_{ass}$ is an association rate constant.

|  | $K_d$ (M)[a] | $k_{ass}$ (M$^{-1}$s$^{-1}$) |
|---|---|---|
| AVD | $(2.1 \pm 0.6) \times 10^{-8}$ | $(2.6 \pm 0.2) \times 10^4$ |
| AVD(I117Y) | $(6.3 \pm 1.2) \times 10^{-8}$ | $(2.3 \pm 0.3) \times 10^4$ |
| ChiAVD | $(1.1 \pm 0.4) \times 10^{-7}$ | $(1.7 \pm 0.1) \times 10^4$ |
| ChiAVD(I117Y) | $(6.7 \pm 1.2) \times 10^{-8}$ | $(1.6 \pm 0.2) \times 10^4$ |
| AVR4/5(C122S) | $(1.4 \pm 0.4) \times 10^{-7}$ | $(9.3 \pm 0.4) \times 10^3$ |

[a]Apparent dissociation constant calculated from equilibrium values

Example 7

Radiobiotin Dissociation Assay

The dissociation rate of [3H]biotin from avidin, AVR4/5 and the avidin mutants was determined as described in (20) at various temperatures. The activation thermodynamic parameters for AVR4/5(C122S) and avidin were determined by analysis of the dependence of the dissociation rate upon temperature using the global fit of all data, as described in (21).

It was found that AVR4/5 binds biotin almost as tightly as avidin. The analysis of the [3H]biotin dissociation data measured at different temperatures revealed that the energy barrier between unbound and bound states in AVR4 is somewhat smaller than in avidin (FIG. 6). The higher free energy of the transition state might also explain the slower association rate to the 2-iminobiotin surface of AVR4 as compared to avidin (FIG. 6, Table III). Because the free energy of the binding is lower in the case of AVR4 (8), the biotin dissociation barrier is still lower for AVR4 despite the higher transition state free energy.

A potential explanation for the differences in biotin-binding characteristics between AVR4/5 and avidin lies in the differences in the L3,4 loop. This region has been found to be an important factor in biotin binding to streptavidin (30). Both the ChiAVD forms showed biotin-binding properties similar to those of AVR4/5 when measured by various methods, therefore supporting this hypothesis. We found that glycosylation may play a minor role in biotin-binding, since AVR4/5(C122S)-b produced in bacteria showed slightly tighter binding characteristics in both the radiobiotin and fluorescent biotin dissociation analyses (FIG. 4, Table IV).

Example 8

Fluorescent Biotin Dissociation Assay

The binding of labelled biotin to avidins was analysed by a method based on the quenching of a biotin-coupled fluorescent probe ArcDia BF560 (ArcDia Ltd., Turku, Finland) due to binding to avidin, as previously described (18). The measurements were performed using a PerkinElmer LS55 luminometer with thermostated cuvette (25 or 50° C.). The signal measured for 3600 sec (25° C.) or 2400 sec (50° C.) was used to determine the dissociation rate constant.

The binding kinetics of the fluorescent biotin conjugate to different avidins were compared by measuring the dissociation rate constants at 25° C. and 50° C. (Table IV). Avidin showed a lower dissociation rate when compared to AVR4/5(C122S). ChiAVD showed characteristics similar to AVR4/5(C122S) in this assay. Interestingly, mutation Ile117Tyr seemed to tighten the binding of the biotin-conjugate to proteins.

Ligand-binding analyses done with a IAsys optical biosensor showed a slightly decreased affinity to the 2-iminobiotin surface in the case of ChiAVD as compared to avidin (Table III). However, the affinity was nonetheless high resembling the values found for AVR4/5(C122S) (8). We also observed a slight decrease in the association rate constants of both ChiAVD-forms as compared to avidin and AVD(I117Y).

AVR4/5(C122S) showed tight biotin binding in the radiobiotin dissociation assay (FIG. 4). However, the measured dissociation rate constants were significantly higher than those of avidin. ChiAVD and ChiAVD(I117Y) resembled AVR4/5(C122S) in this assay. Interestingly, bacterial AVR4/5(C122S)-b showed a slightly slower dissociation rate in this assay than AVR4/5(C122S) produced in insect cells. Avidin mutant AVD(I117Y) showed very tight, avidin-like biotin binding. The activation thermodynamic parameters were calculated from the data as described elsewhere (21) and combined with the thermodynamic parameters obtained for AVR4/5(C122S) and avidin in a previous study (8). The values obtained are shown in FIG. 6.

The dissociation rates observed in the fluorescent biotin assay were significantly faster than those obtained from the radiobiotin analysis, but the proteins nevertheless showed similar relative characteristics (Table IV).

TABLE IV

Biotin-conjugate dissociation kinetics. Dissociation rate constants measured for biotin-BF560-conjugate by a luminometer at 25° C. and at 50° C. The total releases of the probe after measurement for one hour are also shown. $k_{diss}$ is a dissociation rate constant.

|  | $k_{diss}$ ($10^{-5}$ s$^{-1}$) 25° C. | Release 1 h (%) 25° C. | $k_{diss}$ ($10^{-4}$ s$^{-1}$) 50° C. | Release 1 h (%) 50° C. |
|---|---|---|---|---|
| AVD | 2.04 | 10.7 | 2.74 | 71.5 |
| AVD(I117Y) | 0.81 | 3.0 | 1.61 | 56.5 |
| ChiAVD | 1.76 | 13.1 | 8.00 | 93.9 |
| ChiAVD(I117Y) | 1.94 | 9.5 | 7.33 | 94.8 |
| AVR4/5(C122S) | 2.77 | 12.5 | 7.88 | 93.7 |
| AVR4/5(C122S)-b | 2.31 | 10.9 | 6.20 | 88.3 |

Example 9

3-D Structure Analysis

The information obtained from the avidin (24) and AVR4/5(C122S) (Eisenberg-Domovich et al., manuscript) X-ray structures suggested, that the introduction of β4 and its adjacent L3,4 and L4,5 loops from AVR4/5 to avidin cause no crucial change in the overall shape of the resulting protein. The different conformation of the L3,4 loop of AVR4/5 (FIG. 5), when compared to that of avidin, should be analogously reflected in the properties of ChiAVD, namely in a lower number of hydrogen bonds to the bound ligand (Eisenberg-Domovich et al., manuscript). Furthermore, the interchanged sequence includes the two-residue deletion in loop L4,5, which has observed not to change the structural properties of the surrounding region of the loop in AVR4/5 (Eisenberg-Domovich et al., manuscript).

The invention has been illustrated by examples and embodiments, but it may be varied in many ways. Such variations are not to be regarded as a departure from the spirit and scope of the invention and all such modifications are intended to be included within the scope of the enclosed claims.

REFERENCES

1. Green, N. M. (1975) Adv Prot Chem 29, 85-133
2. Green, N. M. (1990) Methods Enzymol 184, 51-67.
3. Wilchek, M., and Bayer, E. A. (1999) Biomol Eng 16,1-4.
4. Wilchek, M., and Bayer, E. (1990) Meth Enzymol 184, 5-13
5. Ahlroth, M. K., Kola, E. H., Ewald, D., Masabanda, J., Sazanov, A., Fries, R., and Kulomaa, M. S. (2000) Anim Genet 31, 367-375.
6. Tuohimaa, P., Joensuu, T., Isola, J., Keinanen, R., Kunnas, T., Niemela, A., Pekki, A., Wallen, M., Ylikomi, T., and Kulomaa, M. (1989) Int J Dev Biol 33, 125-134.
7. Laitinen, O. H., Hytonen, V. P., Ahlroth, M. K., Pentikäinen, O. T., Gallagher, C., Nordlund, H. R., Ovod, V., Marttila, A. T., Porkka, E., Heino, S., Johnson, M. S., Airenne, K. J., and Kulomaa, M. S. (2002) Biochem J 363, 609-617
8. Hytonen, V. P., Nyholm, T. K., Pentikainen, O. T., Vaarno, J., Porkka, E. J., Nordlund, H. R., Johnson, M. S., Slotte, J. P., Laitinen, O. H., and Kulomaa, M. S. (2004) J Biol Chem 279, 9337-9343
9. Backmann, J., Schafer, G., Wyns, L., and Bonisch, H. (1998) J Mol Biol 284, 817-833
10. Villeret, V., Clantin, B., Tricot, C., Legrain, C., Roovers, M., Stalon, V., Glansdorff, N., and Van Beeumen, J. (1998) Proc Natl Acad Sci USA 95, 2801-2806
11. Knapp, S., de Vos, W. M., Rice, D., and Ladenstein, R. (1997) J Mol Biol 267, 916-932
12. Britton, K. L., Yip, K. S., Sedelnikova, S. E., Stillman, T. J., Adams, M. W., Ma, K., Maeder, D. L., Robb, F. T., Tolliday, N., Vetriani, C., Rice, D. W., and Baker, P. J. (1999) J Mol Biol 293,1121-1132
13. Szilagyi, A., and Zavodszky, P. (2000) Structure Fold Des 8, 493-504.
14. Vetriani, C., Maeder, D. L., Tolliday, N., Yip, K. S.-P., Stillman, T. J., Britton, K. L., Rice, D. W., Klump, H. H., Robb, F. T. (1998) Prot. Natl. Acad. Sci. USA 95, 12300-12305
15. Kannan, N., and Vishveshwara, S. (2000) Protein Eng 13, 753-761
16. Serrano, L., Bycroft, M., and Fersht, A. R. (1991) J Mol Biol 218,465-475
17. Sarkar, G., and Sommer, S. S. (1990) Biotechniques 8, 404-407.
18. Hytönen, V. P., Laitinen, O. H., Airenne, T. T., Kidron, H., Meltola, N.J., Porkka, E., Hörhä, J., Paldanius, T., Määttä, J. A., Nordlund, H. R., Johnson, M. S., Salminen, T. A., Airenne, K. J., Ylä-Herttuala, S., and Kulomaa, M. S. (2004) Biochem J 384, 385-390
19. Laitinen, O. H., Marttila, A. T., Airenne, K. J., Kulik, T., Livnah, O., Bayer, E. A., Wilchek, M., and Kulomaa, M. S. (2001) J Biol Chem 276, 8219-8224.
20. Klumb, L. A., Chu, V., and Stayton, P. S. (1998) Biochemistry 37, 7657-7663
21. Hyre, D. E., Le Trong, I., Freitag, S., Stenkamp, R. E., and Stayton, P. S. (2000) Protein Sci 9, 878-885.
22. Gonzalez, M., Argarana, C. E., and Fidelio, G. D. (1999) Biomol Eng 16, 67-72.
23. Nordlund, H. R., Laitinen, O. H., Uotila, S. T., Nyholm, T., Hytonen, V. P., Slotte, J. P., and Kulomaa, M. S. (2003) J Biol Chem 278, 2479-2483.
24. Livnah, O., Bayer, E. A., Wilchek, M., and Sussman, J. L. (1993) Proc Natl Acad Sci USA 90, 5076-5080
25. Thompson, M. J., and Eisenberg, D. (1999) J Mol Biol 290, 595-604.
26. Clackson, T., and Wells, J. A. (1995) Science 267, 383-386.
27. DeLano, W. L. (2002) Curr Opin Struct Biol 12, 14-20.
28. Hu, Z., Ma, B., Wolfson, H., and Nussinov, R. (2000) Proteins 39, 331-342
29. Ahlroth, M. K., Ahlroth, P., and Kulomaa, M. S. (2001) Biochem Biophys Res Commun 288,400-406.
30. Chu, V., Freitag, S., Le Trong, I., Stenkamp, R. E., and Stayton, P.S. (1998) Protein Sci 7, 848-859.
31. Chilkoti, A., Tan, P. H., and Stayton, P. S. (1995) Proc Natl Acad Sci USA 92, 1754-1758.
32. Laitinen, O. H., Airenne, K. J., Marttila, A. T., Kulik, T., Porkka, E., Bayer, E. A., Wilchek, M., and Kulomaa, M. S. (1999) FEBS Lett 461, 52-58
33. Ellison, D., Hinton, J., Hubbard, S. J., and Beynon, R. J. (1995) Protein Sci 4, 1337-1345.
34. Weber, P. C., Ohlendorf, D. H., Wendoloski, J. J., and Salemme, F. R. (1989) Science 243, 85-88
35. Wang, C., Eufemi, M., Turano, C., and Giartosio, A. (1996) Biochemistry 35, 7299-7307.
36. Johnson, M. S., Overington, J. P., and Blundell, T. L. (1993) J Mol Biol 231, 735-752.
37. Ferrin, T. E., Huang, C. C., Jarvis, L. E., and Langridge, R. (1988) J. Mol. Graphics 6, 36-37
38. Marttila, A., Airenne, K., Laitinen, O., Kulik, T., Bayer, E., Wilchek, M., and Kulomaa, M. (1998) FEBS Lett 441, 313-317
39. Nardone, E., Rosano, C., Santambrogio, P., Curnis, F., Corti, A., Magni, F., Siccardi, A. G., Paganelli, G., Losso, R., Apreda, B., Bolognesi, M., Sidoli, A., and Arosio, P. (1998) Eur J Biochem 256, 453-460.

SEQUENCE LISTING

<160> NUMBER OF SEQ ID NOS: 16

<210> SEQ ID NO 1
<211> LENGTH: 420
<212> TYPE: DNA

<213> ORGANISM: Gallus gallus

<400> SEQUENCE: 1

| | | | | | |
|---|---|---|---|---|---|
| gaattccgca | aggagcacac | ccggctgtcc | acctgctgca | gagatggtgc | acgcaacctc | 60 |
| cccgctgctg | ctgctgctgc | tgctcagcct | ggctctggtg | gctcccggcc | tctctgccag | 120 |
| aaagtgctcg | ctgactggga | aatggaccaa | cgatctgggc | tccaacatga | ccatcggggc | 180 |
| tgtgaacagc | agaggtgaat | tcacaggcac | ctacatcaca | gccgtaacag | ccacatcaaa | 240 |
| tgagatcaaa | gagtcaccac | tgcatggaca | caaaacacc | atcaacaaga | ggacccagcc | 300 |
| caccttggc | ttcaccgtca | attggaagtt | ttcagagtcc | accactgtct | tcacgggcca | 360 |
| gtgcttcata | gacaggaatg | ggaaggaggt | cctgaagacc | atgtggctgc | tgcggtcaag | 420 |

<210> SEQ ID NO 2
<211> LENGTH: 1335
<212> TYPE: DNA
<213> ORGANISM: Gallus gallus

<400> SEQUENCE: 2

| | | | | | |
|---|---|---|---|---|---|
| gaattctagg | gacccgatcc | acctgctggt | gagtttgata | ttcgtctctg | gtcttcaatt | 60 |
| ttggggttgt | gcgttcaact | ggaaaacgtg | acccacccag | attgcgtaac | acctgggaag | 120 |
| aaaagcctgc | gccgggagca | ataaaaggcg | agggagcagg | caggaggggt | gagtcctgca | 180 |
| aggagcacac | ccggctgtcc | acctgctgca | gagatggtgc | acgcaacctc | cccgctgctg | 240 |
| ctgctgctgc | tgctcagcct | ggctctggtg | gctcctggcc | tctctgccag | aaagtaatg | 300 |
| gggtggggct | gggagtgggt | gcacctggtg | cccaccctg | cctcctgccc | gccactgact | 360 |
| ccttcttctt | cgtcacagtg | ctcgctgact | gggaaatggg | acaacgacct | gggctccatc | 420 |
| atgaccatcg | gagctgtgaa | cgacaatggc | gagttcaatg | gcacctacat | acagctgta | 480 |
| gcagataatc | caggaaacat | cacgcgatca | ccactgcttg | ggatccaaca | caaaagagcc | 540 |
| tgccagccca | cctttggctt | cactgtccat | tggaactttt | caggtgcttc | tctcccagcc | 600 |
| tccctgcagt | gtccctgctc | ctctgctgtg | cttccctgtg | acaaaccct | ttgctttcct | 660 |
| gcccttcccc | acgctgtctc | cagtgctcgc | ctgcccttcc | ctacagactc | cctgacggtc | 720 |
| tctcctcctc | actgtggtgt | ccctgatgat | ttccagccca | tccctgcagt | ccctcaaca | 780 |
| atgccctgcc | tccatgccc | ccggtgctgc | cccatccctt | cccgtagagc | tgctgggctg | 840 |
| ctgtcacctc | ctggtccccg | ggtgcagggg | aggtgctggg | gctgtcccca | gagggcacgg | 900 |
| agagctcaga | tgagttgtcc | cctgggcaga | gggaccgtgg | tgctggcact | gccctgccct | 960 |
| gcgtggggct | cacaacccca | ctcccctcat | ctgcccctttt | tcccaacaga | gtccaccagt | 1020 |
| gtctttgtgg | gccagtgctt | cgtggacaag | agtggaaagg | aggtcctgaa | gaccaaatgg | 1080 |
| ctgcaacggt | tagcagttga | tgacattagt | gatgactgga | aagctaccag | gtgagcccag | 1140 |
| ggcagaggca | cacggtccca | ggctgtgact | cgatggctgt | gcacttccca | ccttacatct | 1200 |
| cctctctctc | cccgcagggt | cggcaacaac | gacttcactc | gccagcgcac | agtggaggag | 1260 |
| tgaggatggc | cccgcaaagc | cagcaacaat | gccggagtgc | tgacactgct | tgtgatattc | 1320 |
| ctcccaataa | agctt | | | | | 1335 |

<210> SEQ ID NO 3
<211> LENGTH: 1335
<212> TYPE: DNA
<213> ORGANISM: Gallus gallus

<400> SEQUENCE: 3

-continued

```
gaattctaga gacccgatcc acctgctggt gagtttgata ttcgtctctg gtcttcaatt      60
ttggggttgt gcgttcaact ggaaaacgtg acccacccag attgcgtaac acctgggaag     120
aaaagcctgc gccgggagca ataaaaggcg agggagcagg caggaggggt gagtcctgca     180
aggagcacac ccggctgtcc acctgctgca gagatggtgc acgcaacctc ccgctgctg      240
ctgctgctgt tgctcagcct ggctctggtg ctcccagcc tctctgccag aaaggtaacg     300
ggatggggct gggagtgggt gcacctggtg cccaccactg cctcctgccc gccactgact    360
ccttcttctt cactgcagtg ctcgctgact ggggaatggg acaacgacct gggctccatc    420
atgaccatcg gagctgtgaa cgacaatggc gagttcgatg gcacctacat cacagctgta   480
gcagataatc caggaaacat cacgctatca ccactgcttg ggatccaaca caaaagagcc    540
agccagccca cttttggctt cactgtccat tggaactttt caggtgcttc tctcccagcc    600
tccctgcaat gtccctgctc ctctgctgtg cttccctgtg acaaacccct ctgctttcct    660
gcccttcccc acgctgtctc cagtgctctc ctgcccttcc ctacagtctc cctgacggtc    720
tctcctcctc gctgtggtgt ccctgatgat ttccagccct tccctgcaat ccctcaaca    780
atgccctgcc tcccatgccc ccggtgctgc cccatcccctt cccgtagagc tgctgggctg   840
ctgtcacctc caggtccccg ggtgcagggg aagtgctggg gctgtcccca gagggcacag   900
agagctcaga tgagttgtcc cctgggcaga gggaccatgg cactggcact gccctgccct   960
gcgtggggct cacaacccca ctcccctcat ctgccccttt tcccaacaga gtccaccagt  1020
gtctttgtgg gccagtgctt cgtggacagg agcggaaagg aggtcctgaa gaccaaatgg  1080
ctgcaacggt tagcagttga tgacattagt gatgactgga tagctaccag gtgagcccag  1140
ggcagaggca cacggtcccg ggctgtgact cgatggctgt gcacttccca ccttacatct  1200
cctctctctc cccgcagggt cggcaacaac gacttcactc gccagcacac agtggaagag  1260
tgaggatggc cccgcaaagc cagcaacaat gccagagtgc tgacactgct tgtgatattc  1320
ctcccaataa agctt                                                      1335
```

<210> SEQ ID NO 4
<211> LENGTH: 1133
<212> TYPE: DNA
<213> ORGANISM: Gallus gallus

<400> SEQUENCE: 4

```
cctgctgcag agatggtgca cacaacctcc ccgctgctgc tgctgctgct gctcagcctg      60
gctctggtgg ctcccagcct ctctgccaga aaggtaacgg gatggggctg ggagtgggtg    120
cacctggtgc ccaccactgc ctcctgcccg ccactgactc cttcttcttc attgcagtgc   180
tcgctgactg ggaaatggac caacaacctg gctccatca tgaccatcag gctgtgaac    240
agcagaggtg aattcgcagg cacctacctc acagctgtag cagataatcc aggaaacatc   300
aagctatcac cactgcttgg gatccaacac aaaagagcct gccagcccac ctttggcttc   360
actgtccatt ggaacttttc aggtgcttct ctcccagcct ccctgcagtg tccctgctcc   420
tctgctgtgc ttccctgtga caaacccctc tgctttcctg cccttcccca cgctgtctcc   480
agtgctctcc tgcccttccc tacagtctcc ctgacggtct ctcctcctcg ctgtggtgtc   540
cctgatgatt tccagctcat ccctgcaatc ccctcaacaa tgccctgcct cccatgcccc   600
cggtgctgcc ccatcccttc ccgtagagct gctgggctgc tgtcacctcc tggtccccgg   660
gtgcagggga ggtgctgggg ctgtccccag agggcacaga gagctcagat gagttgtccc   720
```

```
ctgggcagag ggaccgtggt gctggcactg tcctgccctg cgtggggctc acgaccccac    780 tccccctcatc tgcccctttt cccacagagt ccaccagtgt ctttgtgggc cagtgcttca    840
tagacaggag cggaaaggag gtcctgaaga ccaaatggct gcaacggtta gcagttgatg    900
acattagtga tgactggaaa gctaccaggt gagcccaggg cagaggcaca cggtcccggg    960
ctgtgactcg atggctgtgc acttcccacc ttacatctcc tctctctccc cgcagggtcg   1020
gctacaacaa cttcactcgc cagcgcacag tggaggagtg aggatggccc cgcaaagcca   1080
gcaacaatgc cggagtgctg acactgcttg tgatattcct cccaataaag ctt         1133
```

```
<210> SEQ ID NO 5
<211> LENGTH: 517
<212> TYPE: DNA
<213> ORGANISM: Gallus gallus

<400> SEQUENCE: 5
cctgctgcag agatggtgca cacaacctcc ccgctgctgc tgctgctgct gctcagcctg     60
gctctggtgg ctcccagcct ctctgccaga aagtgctcgc tgactgggaa atggaccaac    120
aacctgggct ccatcatgac catcagggct gtgaacagca gaggtgaatt cacaggcacc    180
tacctcacag ctgtagcgga taatccagga acatcacgc tatcaccact gcttgggatc     240 caaacacaaaa gagccagcca gcccaccttt ggcttcactg tccattggaa cttttcagag    300
tccaccactg tcttcacggg ccagtgcttc atagacagga acgggaagga ggtcctgaag    360
accatgtggc tgctgcggtc aagtgttaat gacattagtt atgactggaa agctaccagg    420
gtcggctaca caacttcac tcgcctgtgc acagtggagg agtgaggatg ccccgcaaaa    480
gccagcaaca atgccagagt gctgacactg cttgtga                             517
```

```
<210> SEQ ID NO 6
<211> LENGTH: 1334
<212> TYPE: DNA
<213> ORGANISM: Gallus gallus

<400> SEQUENCE: 6
gaattctaga gacccgatcc acctgctggt gagtttgata ttcgtctctg gtcttcaatt     60
ttggggttgt gcgttcaact ggaaaacgtg acccacccag attgcgtaac acctgggaag    120
aaaagcctgc gccgggagca ataaaaggcg agggagcagg caggaggggt gagtcctgca    180
aggagcacac ccggctgtcc acctgctgca gagatggtgc acacaacctc cccgctgctg    240
ctgctgctgc tgctcagcct ggctctggtg gctcccagcc tctctgccag aaagtgaacg    300
ggatggggct gggagtgggt gcacctggtg cccaccactg cctcctgccc gccactgact    360
ccttcttctt cattgcagtg ctcgctgact gggaaatgga ccaacaacct gggctccatc    420
atgaccatca gggctgtgaa cagcagaggt gaattcacag gcacctacct cacagctgta    480
gcggataatc caggaaacat cacgctatca ccactgcttg gatccaaca caaaagagcc    540 agccagccca cctttggctt cactgtccat tggaactttt caggtgcttc tctcccagcc    600
tccctgcagt gtccctgctc ctctgctgtg cttccctgtg acaaacccct ctgctttcct    660
gcccttcccc acgctgtctc cagtgctctc ctgcccttcc ctacagtctc cctgacggtc    720
tctcctcctc gctgtggtgt ccctgatgat ttcagcccca tccctgcagt ccctcaaca    780 atgccctgcc tccatgccc ccggtgctgc ccatcccttt ccgtagagc tgctgggctg     840 ctgtcacctc caggtccccg ggtgcagggg aggtgctggg gctgtcccca gagggcacag    900
agagctcaga tgagttgtcc cctgggcaga gggaccatgg cactggcact gccctgccct    960
```

```
gcgtggggct cacaaccccca ctcccctcat ctgccccttt tcccacagag tccaccactg   1020
tcttcacggg ccagtgcttc atagacagga acgggaagga ggtcctgaag accatgtggc   1080
tgctgcggtc aagtgttaat gacattagtt atgactggaa agctaccagg tgagcccagg   1140
gcagaagcac acggtcccgg gctgtgactc aatggctgtg cacttcccac cttacatctc   1200
ctcactctcc ccgcagggtc ggctacaaca acttcactcg cctgtgcaca gtggaggagt   1260
gaggatggcc ccgcaaagcc agcaacaatg ccagagtgct gacactgctt gtgatattcc   1320
tcccaataaa gctt                                                     1334
```

<210> SEQ ID NO 7
<211> LENGTH: 1133
<212> TYPE: DNA
<213> ORGANISM: Gallus gallus

<400> SEQUENCE: 7

```
cctgctgcag agatggtgca cgcaacctcc ccgctgctgc tgctgctgct gctcagcctg     60
gctctggtgg ctcccggcct ctctgccaga aaggtaacgg gatggggctg ggagtgggtg    120
cacctggcgc ccaccccctgc ctcctgcctg ccactgactc cttcttcttc gtcacagtgc   180
tcgctgactg gggaatggga caacaacctg ggctccatca tgaccatcgg agctgtgaac    240
gacaatggcg agttcaatgg cacctacatc acagctgtag cagataatcc aggaaacatc    300
aagctatcac cactgcttgg gatccaacac aaaagagcct gccagcccac ctttggcttc    360
actgtccatt ggaactttc agtgcttct ctcccagcct ccctgcaatg tccctgctcc      420
tctgctgtgc ttccctgtga caaacccctc tgctttcctg cccttcccca cgctgtctcc    480
agtgctctcc tgcccttccc tacagtctcc ctgacggtct ctcctcctcg ctgtggtgtc   540
cctgatgatt tccagcccat ccctgcagtc ccctcaacaa tgccctgcct cccatgcccc   600
cggtgctgcc ccatcccttc ccgtagagct gctgggctgc tgtcacctcc tggtccccgg   660
gtgcagggga ggtgctgggg ctgtccccag agggcacgga gagctcagat gagttgtccc    720
ctgggcagag ggaccgtggt gctggcactg ccctgccctg cgtggggctc acaaccccac    780
tcccctcatc tgccccttttt cccacagagt ccaccagtgt ctttgtgggc cagtgcttcg   840
tggacaggag cggaaaggag gtcctgaaga ccaaatggct gcaacggtta gcagttgatg    900
acattagtga tgactggaaa gctaccaggt gagcccaggg cagaggcaca cggtcccggg    960
ctgtgactcg atggctgtgc acttcccacc ttacatctcc tctctctccc cgcagggtcg   1020
gctacaacaa cttcactcgc cagcgcacag tggaggagtg aggatggccc cgcaaagcca   1080
gcaacaatgc cggagtgctg acactgcttg tgatattcct cccaataaag ctt          1133
```

<210> SEQ ID NO 8
<211> LENGTH: 1133
<212> TYPE: DNA
<213> ORGANISM: Gallus gallus

<400> SEQUENCE: 8

```
cctgctgcag agatggtgca cgcaacctcc ccgctgctgc tgctgctgct gctcagcctg     60
gctctggtgg ctcccggcct ctctgccaga aaggtaacgg gatggggctg ggagtgggtg    120
cacctggtgc ccaccccctgc ctcctgcctg ccactgactc cttcttcttc gtcacagtgc   180
tcgctgactg gggaatggga caacaacctg ggctccaaca tgaccatcgg agctgtgaac    240
gacaatggcg agttcaatgg cacctacatc acagctgtag cagataatcc aggaaacatc    300
```

-continued

```
aagctatcac cactgcttgg gatccaacac aaaagagcct gccagcccac ctttggcttc        360
actgtccatt ggaacttttc aggtgcttct ctcccagcct ccctgcagtg tccctgctcc        420
tctgctgtgc ttccctgtga caaaccsctc tgctttcctg cccttcccca cgctgtctcc        480
agtgctctcc tgcccttccc tacagtctcc ctgacggtct ctcctcctcg ctgtggtgtc        540
cctgatgatt tccagctcat ccctgcaatc ccctcaacaa tgccctgcct cccatgcccc        600
cggtgctgcc ccatccctt c ccgtagagct gctgggctgc tgtcacctcc tggtccccgg        660
gtgcagggga ggtgctgggg ctgtccccag agggcacaga gagctcagat gagttgtccc        720
ctgggcagag ggaccgtggt gctggcactg tcctgccctg cgtggggctc acgaccccac        780
tcccctcatc tgcccctttt cccacagagt ccaccagtgt ctttgtgggc cagtgcttca        840
tagacaggag cggaaaggag gtcctgaaga ccaaatggct gcaacggtta gcagttgatg        900
acattagtga tgactggaaa gctaccaggt gagcccaggg cagaggcaca cggtcccggg        960
ctgtgactcg atggctgtgc acttcccacc ttacatctcc tctctctccc cgcagggtcg       1020
gctacaacaa cttcactcgc cagcgcacag tggaggagtg aggatggccc cgcaaagcca       1080
gcaacaatgc cggagtgctg acactgcttg tgatattcct cccaataaag ctt             1133
```

```
<210> SEQ ID NO 9
<211> LENGTH: 37
<212> TYPE: DNA
<213> ORGANISM: Artificial sequence
<220> FEATURE:
<223> OTHER INFORMATION: template

<400> SEQUENCE: 9
gcacctacat cacagccgta gcggataatc caggaaa                                  37

<210> SEQ ID NO 10
<211> LENGTH: 37
<212> TYPE: DNA
<213> ORGANISM: Artificial sequence
<220> FEATURE:
<223> OTHER INFORMATION: template

<400> SEQUENCE: 10
gaagccaaag gtgggctggc tggctctttt gtgttgg                                  37

<210> SEQ ID NO 11
<211> LENGTH: 31
<212> TYPE: DNA
<213> ORGANISM: Artificial sequence
<220> FEATURE:
<223> OTHER INFORMATION: oligonucleotide

<400> SEQUENCE: 11
ctgctagatc tatggtgcac gcaacctccc c                                        31

<210> SEQ ID NO 12
<211> LENGTH: 24
<212> TYPE: DNA
<213> ORGANISM: Artificial sequence
<220> FEATURE:
<223> OTHER INFORMATION: oligonucleotide

<400> SEQUENCE: 12
gttgcaagct ttgcggggcc atcc                                                24

<210> SEQ ID NO 13
<211> LENGTH: 22
```

```
<212> TYPE: DNA
<213> ORGANISM: Artificial sequence
<220> FEATURE:
<223> OTHER INFORMATION: oligonucleotide

<400> SEQUENCE: 13
cagggtcggc tacaacatct tc                                          22

<210> SEQ ID NO 14
<211> LENGTH: 22
<212> TYPE: DNA
<213> ORGANISM: Artificial sequence
<220> FEATURE:
<223> OTHER INFORMATION: oligonucleotide

<400> SEQUENCE: 14
gaagatgttg tagccgaccc tg                                          22

<210> SEQ ID NO 15
<211> LENGTH: 453
<212> TYPE: DNA
<213> ORGANISM: Gallus gallus

<400> SEQUENCE: 15
atggtgcacg caacctcccc gctgctgctg ctgctgctgc tcagcctggc tctggtggct    60
cccggcctct ctgccagaaa gtgctcgctg actgggaaat ggaccaacga tctgggctcc   120
aacatgacca tcgggctgt gaacagcaga ggtgaattca caggcaccta tatcacagcc   180
gtagcggata atccaggaaa catcacgcta tcaccactgc ttgggatcca acacaaaaga   240
gccagccagc ccacctttgg cttcaccgtc aattggaagt tttcagagtc caccactgtc   300
ttcacgggcc agtgcttcat agacaggaat gggaaggagg tcctgaagac catgtggctg   360
ctgcggtcaa gtgttaatga cattggtgat gactggaaag ctaccagggt cggcatcaac   420
atcttcactc gcctgcgcac acagaaggag tga                                453

<210> SEQ ID NO 16
<211> LENGTH: 150
<212> TYPE: PRT
<213> ORGANISM: Gallus gallus

<400> SEQUENCE: 16

Met Val His Ala Thr Ser Pro Leu Leu Leu Leu Leu Leu Ser Leu
1               5                   10                  15

Ala Leu Val Ala Pro Gly Leu Ser Ala Arg Lys Cys Ser Leu Thr Gly
            20                  25                  30

Lys Trp Thr Asn Asp Leu Gly Ser Asn Met Thr Ile Gly Ala Val Asn
        35                  40                  45

Ser Arg Gly Glu Phe Thr Gly Thr Tyr Ile Thr Ala Val Ala Asp Asn
    50                  55                  60

Pro Gly Asn Ile Thr Leu Ser Pro Leu Leu Gly Ile Gln His Lys Arg
65                  70                  75                  80

Ala Ser Gln Pro Thr Phe Gly Phe Thr Val Asn Trp Lys Phe Ser Glu
                85                  90                  95

Ser Thr Thr Val Phe Thr Gly Gln Cys Phe Ile Asp Arg Asn Gly Lys
            100                 105                 110

Glu Val Leu Lys Thr Met Trp Leu Leu Arg Ser Ser Val Asn Asp Ile
        115                 120                 125

Gly Asp Asp Trp Lys Ala Thr Arg Val Gly Tyr Asn Ile Phe Thr Arg
    130                 135                 140
```

```
Leu Arg Thr Gln Lys Glu
145             150
```

The invention claimed is:

1. A chimeric protein comprising a chicken avidin amino acid sequence that comprises β1, β2, β3, β4, β5, β6, β7, and β8 avidin structural domains, with the proviso that the β4 structural domain of said avidin amino acid sequence is replaced with a heterologous β4 structural domain that comprises amino acids 38-58 of SEQ ID NO:18, wherein said chimeric protein binds biotin.

2. The chimeric protein of claim 1, wherein said chimeric protein has $T_m$ greater than the $T_m$ of an avidin protein that comprises the chicken avidin amino acid sequence.

3. The chimeric protein of claim 1, wherein the avidin amino acid sequence comprises: (a) the amino acid sequence of SEQ ID NO:17; or (b) the amino acid sequence of SEQ ID NO:17, wherein isoleucine 117 is replaced with a tyrosine (I117Y).

4. The chimeric protein of claim 1, comprising the avidin amino acid sequence set forth in SEQ ID NO:17, with the proviso that the β4 structural domain amino acid residues 38-60 of SEQ ID NO:17 are replaced with amino acid residues 38-58 of SEQ ID NO:18.

5. A chimeric protein comprising the amino acid sequence set forth in SEQ ID NO:17, with the provisos that: the β4 structural domain amino acid residues 38-60 of SEQ ID NO:17 are replaced with amino acid residues 38-58 of SEQ ID NO:18; and isoleucine 117 of SEQ ID NO:17 is replaced with tyrosine (I117Y).

6. A chimeric protein comprising the amino acid sequence of SEQ ID NO: 16.

* * * * *

UNITED STATES PATENT AND TRADEMARK OFFICE
CERTIFICATE OF CORRECTION

PATENT NO. : 7,268,216 B2
APPLICATION NO. : 11/321685
DATED : September 11, 2007
INVENTOR(S) : Vesa P. Hytonen et al.

It is certified that error appears in the above-identified patent and that said Letters Patent is hereby corrected as shown below:

In the Sequence Listing:

In field <160>, please delete "NUMBER OF SEQ ID NOS: 16" and replace it with --NUMBER OF SEQ ID NOS: 18--

At Column 25, immediately following SEQ ID NO: 16, please add SEQ ID NO: 17 and SEQ ID NO: 18 as follows:

--
<210> 17
<211> 128
<212> PRT
<213> Gallus gallus

<400> 17

Ala Arg Lys Cys Ser Leu Thr Gly Lys Trp Thr Asn Asp Leu Gly Ser
1               5                   10                  15

Asn Met Thr Ile Gly Ala Val Asn Ser Arg Gly Glu Phe Thr Gly Thr
            20                  25                  30

Tyr Ile Thr Ala Val Thr Ala Thr Ser Asn Glu Ile Lys Glu Ser Pro
        35                  40                  45

UNITED STATES PATENT AND TRADEMARK OFFICE
CERTIFICATE OF CORRECTION

PATENT NO. : 7,268,216 B2
APPLICATION NO. : 11/321685
DATED : September 11, 2007
INVENTOR(S) : Vesa P. Hytonen et al.

It is certified that error appears in the above-identified patent and that said Letters Patent is hereby corrected as shown below:

Leu His Gly Thr Gln Asn Thr Ile Asn Lys Arg Thr Gln Pro Thr Phe
    50                55                60

Gly Phe Thr Val Asn Trp Lys Phe Ser Glu Ser Thr Thr Val Phe Thr
65              70              75              80

Gly Gln Cys Phe Ile Asp Arg Asn Gly Lys Glu Val Leu Lys Thr Met
          85              90              95

Trp Leu Leu Arg Ser Ser Val Asn Asp Ile Gly Asp Asp Trp Lys Ala
       100           105           110

Thr Arg Val Gly Ile Asn Ile Phe Thr Arg Leu Arg Thr Gln Lys Glu
      115           120           125

<210> 18
<211> 125
<212> PRT
<213> Gallus gallus

<400> 18

Ala Arg Lys Cys Ser Leu Thr Gly Lys Trp Thr Asn Asn Leu Gly Ser
1           5              10              15

Met Thr Ile Arg Ala Val Asn Ser Arg Gly Glu Phe Thr Gly Thr Tyr
       20           25           30

Leu Thr Ala Val Ala Asp Asn Pro Gly Asn Ile Thr Leu Ser Pro Leu
      35          40            45

Leu Gly Ile Gln His Lys Arg Ala Ser Gln Pro Thr Phe Gly Phe Thr
    50            55            60

UNITED STATES PATENT AND TRADEMARK OFFICE
CERTIFICATE OF CORRECTION

PATENT NO. : 7,268,216 B2
APPLICATION NO. : 11/321685
DATED : September 11, 2007
INVENTOR(S) : Vesa P. Hytonen et al.

It is certified that error appears in the above-identified patent and that said Letters Patent is hereby corrected as shown below:

```
Val His Trp Asn Phe Ser Glu Ser Thr Thr Val Phe Thr Gly Gln Cys
65                  70                  75                  80

Phe Ile Asp Arg Asn Gly Lys Glu Val Leu Lys Thr Met Trp Leu Leu
                85                  90                  95

Arg Ser Ser Val Asn Asp Ile Ser Tyr Asp Trp Lys Ala Thr Arg Val
            100                 105                 110

Gly Tyr Asn Asn Phe Thr Arg Leu Ser Thr Val Glu Glu --.
            115                 120                 125
```

Signed and Sealed this

Thirty-first Day of March, 2009

JOHN DOLL
*Acting Director of the United States Patent and Trademark Office*